United States Patent
Morgan

(10) Patent No.: US 6,592,370 B2
(45) Date of Patent: Jul. 15, 2003

(54) ABUTMENT FOR DENTAL IMPLANT AND ASSOCIATED COMPONENTS FOR USE THEREWITH

(75) Inventor: Vincent J. Morgan, Boston, MA (US)

(73) Assignee: Diro, Inc., Boston, MA (US)

( * ) Notice: Subject to any disclaimer, the term of this patent is extended or adjusted under 35 U.S.C. 154(b) by 0 days.

(21) Appl. No.: 09/952,087

(22) Filed: Sep. 11, 2001

(65) Prior Publication Data

US 2002/0031749 A1 Mar. 14, 2002

Related U.S. Application Data

(60) Provisional application No. 60/232,522, filed on Sep. 14, 2000.

(51) Int. Cl.$^7$ ................................. A61C 8/00
(52) U.S. Cl. ..................................... 433/173
(58) Field of Search ................ 433/173, 172, 433/174

(56) References Cited

U.S. PATENT DOCUMENTS

| | | | |
|---|---|---|---|
| 5,749,731 A | 5/1998 | Morgan et al. ............ 433/173 |
| 5,782,918 A * | 7/1998 | Klardie et al. ............... 623/16 |
| 5,863,200 A * | 1/1999 | Hamada et al. ............. 433/173 |
| 6,068,478 A * | 5/2000 | Grande et al. .............. 433/172 |

* cited by examiner

*Primary Examiner*—Kevin Shaver
*Assistant Examiner*—Melba Bumgarner
(74) *Attorney, Agent, or Firm*—John A. Haug

(57) ABSTRACT

An abutment (10, 10A, 10B, 10C) for a medical or dental implant has a prosthetic receiving tapered post formed with a locking step (10e) for removably restraining a sleeve member such as an emergence cuff (12, 12A). The emergence cuff is receivable on the post of the abutment and has an outer surface configuration which merges confluently with the abutment outer surface. The emergence cuff is formed with a snap on interface (12g) for use with a second sleeve (14, 14A) having a complimentary snap on interface (14e). When the second sleeve is open ended, a pin (16) is shown for closing off the outer end of the second sleeve, if desired.

22 Claims, 4 Drawing Sheets

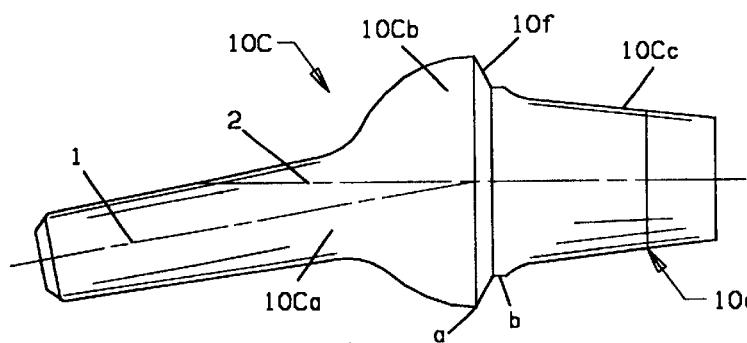
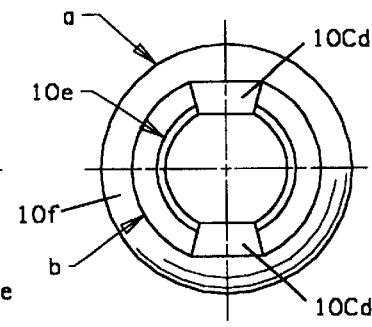
FIG. 4      FIG. 4a
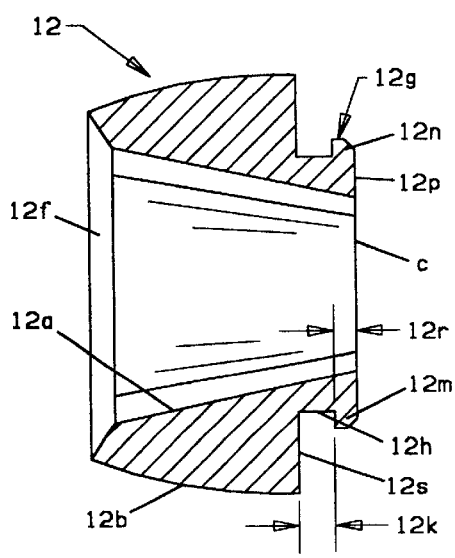
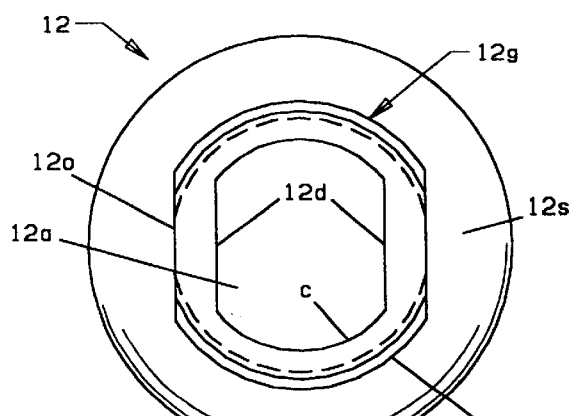
FIG. 5      FIG. 5a
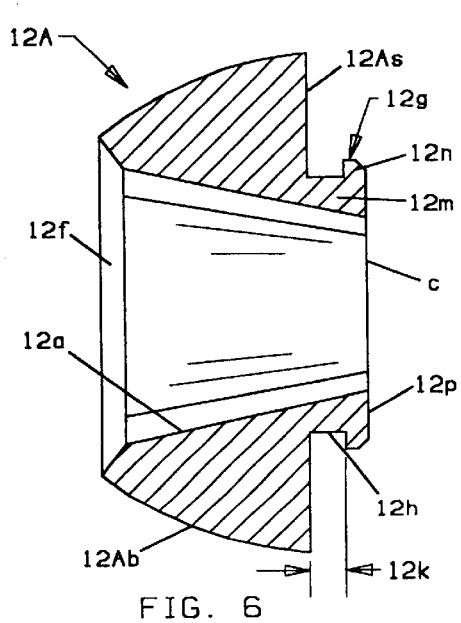
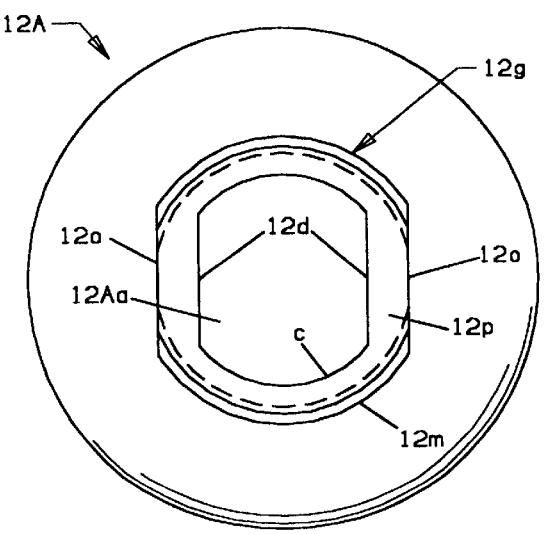
FIG. 6      FIG. 6a

ABUTMENT FOR DENTAL IMPLANT AND ASSOCIATED COMPONENTS FOR USE THEREWITH

CROSS-REFERENCE TO RELATED APPLICATION

Benefit is claimed of Prov. Appl. No. 60/232,522, filed Sep. 14, 2000.

FIELD OF THE INVENTION

This invention relates generally to dental or medical prosthetic implants and more particularly to abutments used with dental implants and associated components used in implant procedures.

BACKGROUND OF THE INVENTION

It is known to place an annular cuff formed of suitable biocompatible material on a permanent abutment member at the time the abutment is mounted on the root member and the gum tissue is then sutured over the cuff and abutment member and allowed to heal, as taught in U.S. Pat. No. 5,749,731, assigned to the assignee of the present invention. After sufficient healing the cuff can be removed leaving a sulcus having a predetermined, optimized shape. The cuff can be formed with an inwardly extending, circumferential lip for placement onto the undercut of the abutment to provide a positive seat for the cuff.

An object of the invention is the provision of a locking mechanism for retention of a first sleeve on an abutment, the sleeve having an outer surface smoothly confluent with the outer surface of the abutment. Another object is the provision of a second sleeve, the first and second sleeves having an interface for locking on to each other. Yet another object of the invention is the provision of a second sleeve having a feature for interlocking with other dental materials.

SUMMARY OF THE INVENTION

Briefly, an abutment system made in accordance with the invention includes an abutment having several versions with various taper post or screw diameters for mounting in a root member, gingival radii, margins, abutment post diameters and abutment post heights. Each abutment post has a retention feature for retaining or locking a member, for example, an emergence cuff or wax-up sleeve. The abutments are formed of biocompatible material such as titanium alloy or ultra-high density polyethylene.

The emergence cuff or first sleeve member, formed of suitable material, such as plastic, is similar to that shown and described in the above mentioned U.S. patent, but adapted for use with the retentive feature of the abutments and provided with an interface for an optional second sleeve member. The second sleeve member, also formed of suitable material, such as plastic, ceramic or metal, snaps onto the first sleeve member and can be used, for example, in making impressions, particularly when provided with an undercut for retention of the second sleeve in impression material.

A sleeve pin, formed of suitable material, such as metal, plastic, ceramic or composite material, can be used for snapping onto the occlusal end of the second sleeve member or used as a one piece sleeve to provide an outer profile for such purposes as impression making, a waxing sleeve, a corrective coping, a jig or for prosthetic fabrication for contouring of the soft tissues and stabilizing of the implant during healing. The pin can be used to temporarily close the sleeve opening and extend the height of the sleeve. A one or two piece sleeve member can have multiple uses, such as: for making impressions, fabricating crowns, modifying abutments and recording relationships, both intra-orally as well as in a laboratory setting. The sleeve member, for example, could actually have the morphology of a tooth, such that it could provide the basis for the transition or final medical or dental prosthesis with specific additions or deletions for a particular restoration.

Additional objects and features of the invention will be set forth in part in the description which follows and in part will be obvious from the description. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings:

FIG. 4 is a front view of a long angled abutment having the second nominal diameter root mounting post and FIG. 4a is a right end view thereof;

FIG. 5 is an enlarged cross section taken through an emergence cuff or first sleeve member and FIG. 5a is a left end view thereof;

FIG. 6 is an enlarged cross section taken through another emergence cuff or first sleeve member and FIG. 6a is a left end view thereof;

DETAILED DESCRIPTION OF THE PREFERRED EMBODIMENTS

Figure 1:
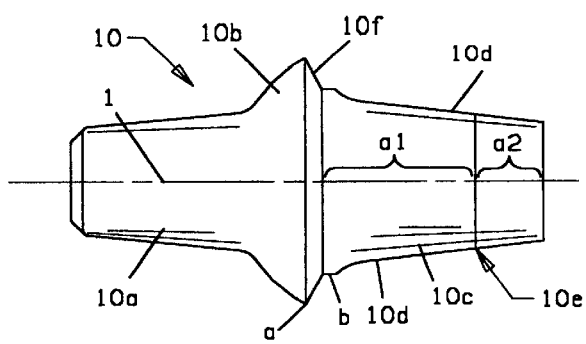
FIG. 1 is a front view of a straight abutment having a first nominal diameter root mounting post.
Figure 1A:
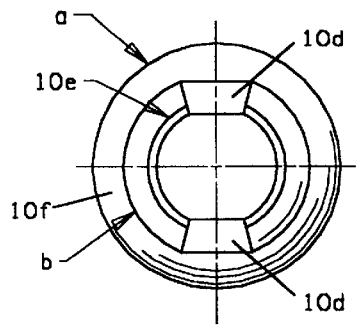
FIG. 1a is a right end view thereof and FIG. 1b is a top, broken away, view of FIG. 1.
Figure 1B:
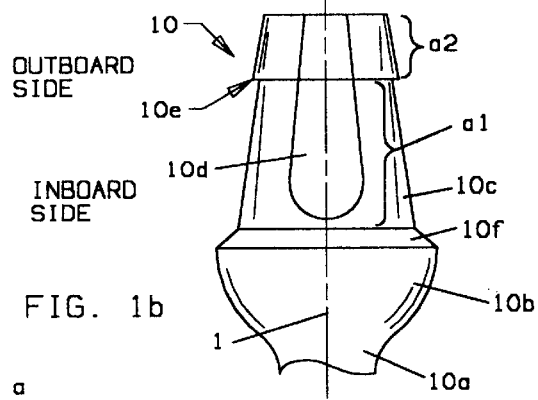
Figure 2:
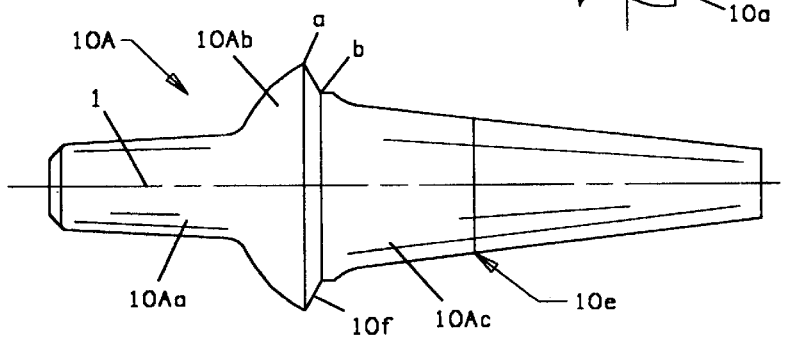
FIG. 2 is a front view of a straight abutment having a second, smaller, nominal diameter root mounting post
Figure 2A:
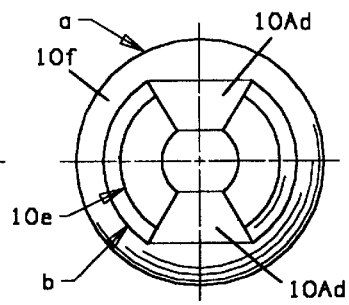
FIG. 2a is a right end view thereof.
Figure 3:
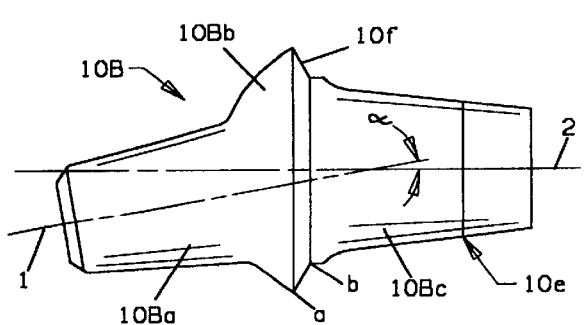
FIG. 3 is a front view of an angled abutment having the second nominal diameter root mounting post and FIG. 3a is a right end view thereof.
Figure 3A:
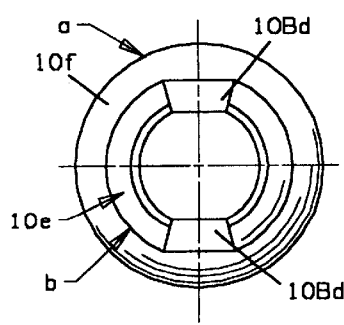

With reference to FIGS. 1, 1a, abutment 10 is shown having a locking tapered mounting portion or post 10a for receipt in an implant or root member (not shown) having a post receiving bore formed with a complimentary locking taper, a basal or central portion 10b and a post 10c having a selected length extending from central portion 10b for mounting of a prosthetic member such as a crown or the like. Post portion 10c generally cylindrical and is preferably formed with a taper one or more anti rotational flats 10d and, as best seen in FIG. 1b, with a stepped locking portion 10e formed intermediate to first and second axial length portions a1, a2 of post 10c for removable retention of a sleeve member to be described below. Stepped portion 10e can be formed to extend completely around the circumference or, if desired, along a portion thereof, such as along the radiused portions of the circumference, as shown. As best seen in FIG. 1b, the circumference of each axial length portion decreases as the distance from the central portion increases. The circumference of the post on the side of step 10e outboard, or further from the central portion immediately adjacent to the step is larger than the circumference of the post on the side of step 10e inboard, or closer to the central portion immediately adjacent to step 10e to form the retention feature.

Abutments can be made with implant receiving posts 10a of the same locking taper but of different lengths, diameters, angles and contours joining the respective basal potion as shown by way of example in FIGS. 1–4. The implant receiving posts 10, 10Aa, 10Bb, and 10Ca of abutments 10A, 10B and 10C, respectively are of a smaller diameter than post 10a. Posts 10Ba and 10Ca are both angled, such as at an angle alpha, between longitudinal axis 1 of the implant receiving post and longitudinal axis 2 of the crown receiving post respectively for use in a locus in which the implant is placed calling for such orientation. The crown receiving posts 10c, 10Ac, 10Bc and 10Cc are all formed with the same outer configuration including the generally frustoconical foot portion 10f, although their lengths can be varied as shown by elongated post 10Ac of FIG. 2. Abutments made in accordance with the invention had crown receiving foot portions having a large diameter "a" of 0.205 mm and a small diameter "b" of 0.158 mm and crown receiving posts formed with a taper of 6 degrees 34 minutes with step 10e having a diameter for the inner or inboard side (the side closest to the central portion) immediately adjacent to the step of between 0.117 and 0.121 mm and the outer or outboard side (the side furthest from the central portion) immediately adjacent to the step of between 0.123 and 0.125 mm.

FIGS. 5, 5a, 6 and 6a show two forms of emergence cuffs or first sleeve members 12 and 12A having a tapered bore 12a of a size and configuration essentially matching that of the crown receiving posts of the abutments described above, including foot portion 12f and flats 12d. The smaller diameter "c" of bore 12a is selected to be slightly smaller than the diameter on the inboard side of step portion 10e, that is, with respect to the specific examples of abutments disclosed above, diameter "c" was selected to be between 0.122 and 0.124 mm so that when placed on the crown receiving post of an abutment made in accordance with the invention the emergence cuff will snap over step portion 10e for removable retention on the post and with foot portion 12f of the emergence cuff received on foot portion 10f of the abutment. The outer configuration 12b, 12Ab, 12Bb and 12Cb of the respective emergence cuffs 12, 12A can be varied as appropriate relative to the desired sulcus profile but preferably will form a smooth confluent surface with the outer configuration of basal portion 10b, 10Ab, 10Bb and 10Cb of the respective abutment.

The outer end of the emergence cuff, that is, the end opposite foot portion 12f may be formed, if desired, with a snap on interface 12g for use with a second sleeve member to be described below. Interface 12g comprises a hub portion including a circumferentially extending groove 12h having a selected width 12k with a radially extending flange 12m defining the groove on the coronal side of the emergence cuff. Flange 12m has a reduced outer diameter relative to the coronal end portion of outer surface portion 12b, 12Ab on the other side of groove 12h for receipt in an opening in a second sleeve member to be described. A chamfered surface 12n is formed on the flange at the outer face for a purpose to be described. Preferably, the flange is formed with anti rotational flats 12o for inter engagement with corresponding anti rotational flats on the second sleeve member. The overall length of emergence cuffs 12, 12A is selected so that when seated on foot 10f of an abutment made in accordance with the invention, the coronal end 12p will be disposed on the inboard side of step 10e.

A second sleeve member 14 is shown in FIGS. 7 and 7a–7c and preferably comprises a generally frustoconical shaped outer body configuration 14a having a first longitudinally extending bore portion 14b which essentially forms a continuation of the bore of the emergence cuff with which the second sleeve member is used and a second longitudinally extending bore portion 14c, preferably having a constant diameter. Interface 14g comprises a recessed flange receiving seat 14d at the inner or larger diameter end having a longitudinally extending width 14e and a diameter 14f. The mouth of the flange receiving seat is formed with a bevel having a diameter ranging from the inner end face of sleeve 14 at 14h to a smaller diameter 14i inboard a selected longitudinal distance 14k, forming a lip 14r. An oppositely angled bevel leads from the lip, i.e., from diameter 14i to the flange seat diameter over a longitudinal distance 14m.

Figure 7A:
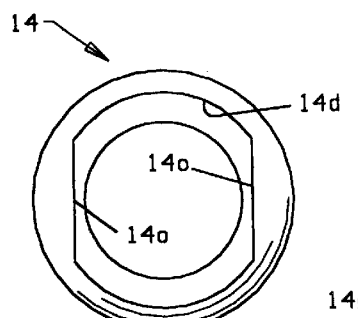
FIG. 7a is a left end view thereof.
Figure 7:
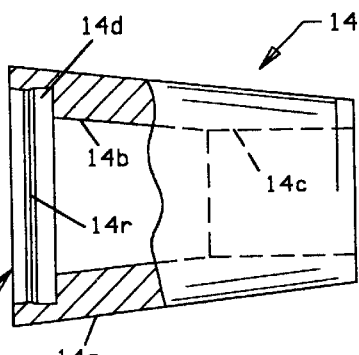
FIG. 7 is a front view, partly in cross section, of a second sleeve receivable on the first sleeve.
Figure 7B:
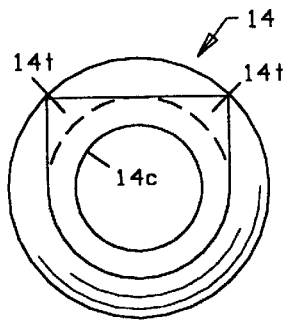
FIG. 7b is a right end view thereof and FIG. 7c is an enlarged, broken away portion of FIG. 7.
Figure 7C:
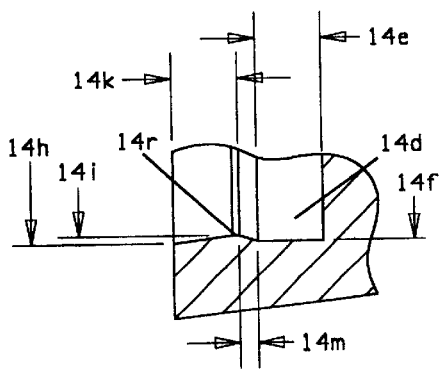
Figure 8:
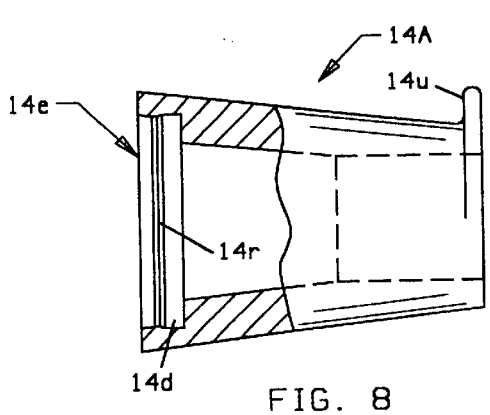
FIG. 8 is another front view of a second sleeve showing details of a cut away portion for locking with impression material.
Figure 9:
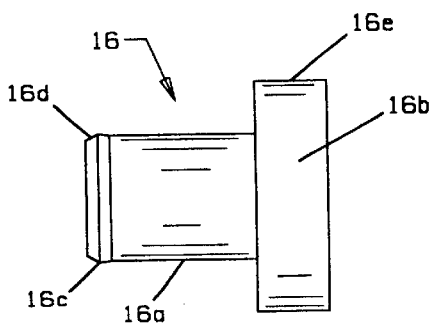
FIG. 9 is a front view of a pin receivable in the outer end of the second sleeve member shown in FIGS. 7 and 8.
Figure 9A:
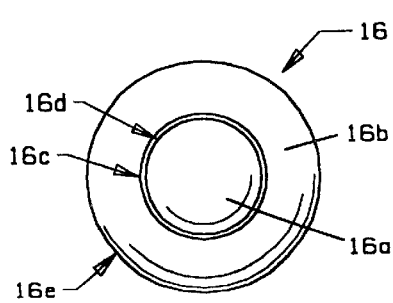
FIG. 9a is a left side view thereof.

Second sleeve 14 is attached to emergence cuff 12 by placing the beveled portion 14k onto flange 12m, the outer diameter of flange 12m preferably being intermediate to diameters 14h, and slightly less than diameter 14f of flange seat 14d. The second sleeve is pushed onto the emergence cuff until flange 12m snaps beyond the smaller diameter portion 14i. The longitudinal width of flange 12k is less than the longitudinal width of flange seat 14d and the longitudinal width of groove 12k is selected so that coronal end face 12s of the emergence cuff and the inner end face of sleeve 14 butt up against each other and the grooved portion extends over the two beveled portions. The flange seat 14d is also formed with anti rotational flats 14o which cooperate with corresponding flats 12o of the emergence cuff. As seen in FIG. 7b, second sleeve 14 is also formed with squared off ear portions 14t for handling. When used for interlocking with impression material the second sleeve can be formed with an undercut 14u as shown in sleeve 14A in FIG. 8. By way of example, emergence cuffs and second sleeve members made in accordance with the invention had the following dimensions relating to the snap on interface:

Emergence cuff 12, 12A:

outer diameter of flange 12m: 0.170/0.169 mm diameter on inner surface of groove 12h: 0.150 mm longitudinal distance 12k of groove: 0.018 mm longitudinal width of flange 12r:0.015 mm Second sleeve member 14, 14A:

diameter 14f of flange seat: 0.171/0.172 nm longitudinal width 14e of flange seat 14d: 0.021/0.018 mm diameter 14h at mouth of flange seat: 0.173/0.174 mm diameter 14i at inner end of outer bevel (lip 14r):0.167/0.168 mm longitudinal distance 14k of outer bevel: 0.010 mm longitudinal distance 14m of inner bevel: 0.004 mm
diameter of bore portion 14c: 0.100 mm FIGS. 9 and 9a show a pin 16 having a body portion 16a and a head 16b with the body portion having a diameter selected to fit in bore 14c at the coronal end of second sleeve 14, 14A to close off the second sleeve when desired. For the second sleeve member examples described above, the diameter of body portion 16b is selected as 0.100 mm, preferably with a distal free end having a radially extending bead with a diameter 16c of 0.102 mm beveled down to a diameter 16d of 0.090 mm. The diameter 16e of head 16b can be selected to be slightly larger than the outer end of second sleeve 14, 14A, if desired. It will be understood that the second sleeve can be formed open ended, as described above, or it could be preformed with a closed end.

Figure 10:
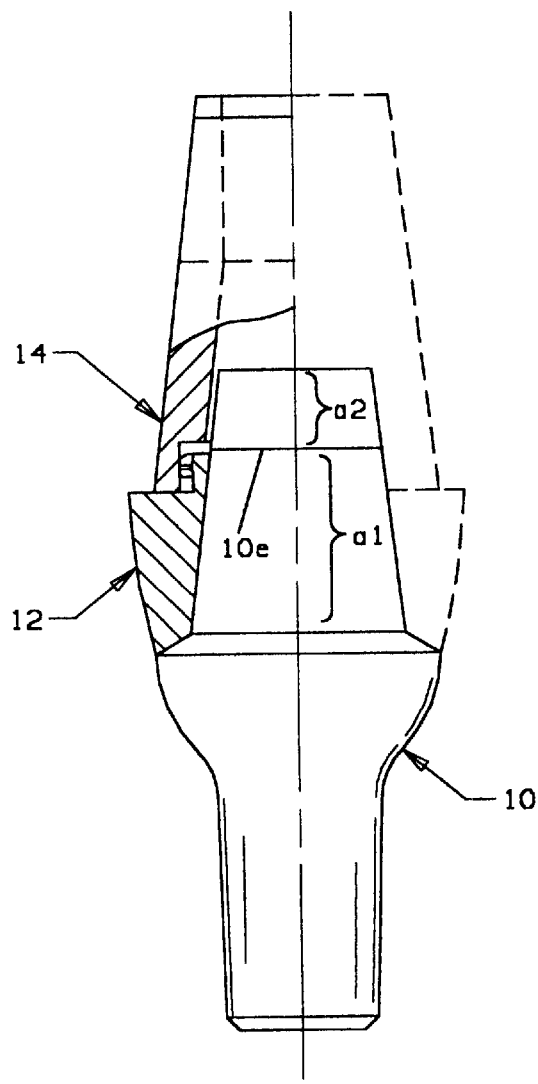
FIG. 10 is a front view of an abutment made in accordance with the invention with both a first and second sleeve, shown partly in cross section and partly in dashed lines, received and removably locked onto the abutment.
Figure 10A:
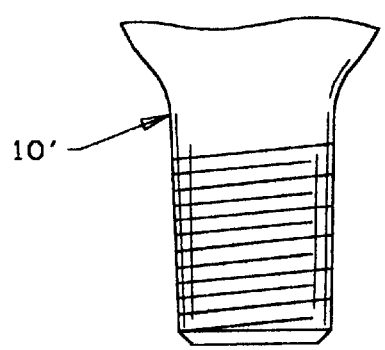
FIG. 10a is a broken away front view of a modified abutment.

FIG. 10 shows an abutment 10 with an emergence cuff or first sleeve member 12 snapped thereon and with a second sleeve member 14 snapped on to the emergence cuff. The outer configuration of the second sleeve can be formed as shown forming a step with the emergence cuff or it could be formed to merge confluently with the emergence cuff, as desired. The abutment is typically formed of titanium or titanium alloy or it could be formed of ultra-high polyethylene or the like when used as a transitional healing abutment while the sleeve members can be formed of metal, plastic or ceramic material, such as: polycarbonate, polyceramic, acrylic, composite, aluminum oxide, polyglass or any other suitably biocompatible material.

The emergence cuff, as noted above, can be used in the same way as that of the above referenced patent. For example, the emergence cuff could form a portion of a temporary crown or, along with the second sleeve member, could serve as an impression post, particularly with the undercut 14u of FIG. 8 so that it would be locked to and withdrawn with impression medium. The emergence cuff facilitates placement of the crown/abutment interface below the gingiva for various depths of gingival tissue existing above the abutment/implant interface.

The second sleeve member, or a one piece sleeve member, is multifuntional, including such functions as facilitating temporization of a fabricated dental or medical prosthesis, recording the geometry of the position of the abutment, actually being incorporated into a dental or medical prosthesis, temporary or permanent, and can be used as a template or jig, or as an abutment to contour the soft tissues or to stabilize the healing implant. The sleeve members can be of various heights and shapes, such as an elliptical shape to replicate a front tooth. The sleeve member can be closed-in and can be readily modified for various clinical situations. The sleeve member may have essentially the same size and shape of a tooth, thus only requiring some modification for a specific clinical situation. It will be understood that for elongated, one piece sleeve members the internal bore would be formed with suitable retention means for interengaging with step portion 10e of the crown receiving post of the abutment, such as a step portion having a mirror image of step portion 10e being located in the bore of the sleeve member at a position selected so that when the sleeve member is seated on the abutment, the mirror image step would interengage with step portion 10e in the same manner that the end portion of emergence cuffs 12, 12A, defined by diameter "c" of the respective emergence cuff, interengages with step portion 10e.

Although the invention has been described with regard to specific preferred embodiments thereof, variations and modifications will become apparent to those skilled in the art. It will be understood that although the emergence cuffs are described above as being removably retained by step portion 10e, when permanent retention of a sleeve member is desired, for example, when used as a prosthetic crown or the like as mentioned above, the member can be permanently attached by augmenting the attachment by cementing or otherwise suitably bonding the member to the crown receiving post of the abutment. It is therefore, the intention that the appended claims be interpreted as broadly as possible in view of the prior art to include all such variations and modifications.

What is claimed:

1. An abutment for use with an implant placed in a bone of a patient comprising an integrally formed mounting portion, central portion and solid prosthetic mounting post, the mounting portion adapted for receipt in an implant, the central portion having a longitudinal axis and a smoothly curved outer surface relative to the longitudinal axis and the prosthetic mounting post extending from the central portion, the post being generally cylindrical and being tapered along a selected length of the post, the selected length having a first and a second axial length portion, each axial length portion having a decreasing circumference as the distance from the central portion increases, the post formed with a locking step disposed intermediate to the first and second axial length portions with one side of the step being outboard, further from the central portion and an opposite side being inboard, closer to the central portion, the post having increased circumference on the outboard side of the step immediately adjacent to the locking step relative to the circumference of the post on the inboard side of the step immediately adjacent to the locking step, the locking step being formed at a given distance from the central portion.

2. An abutment according to claim 1 in which the mounting post is formed with at least one anti rotational flat on the outer periphery thereof.

3. An abutment according to claim 2 in which the locking step extends over the cylindrical portion of the mounting post.

4. An abutment according to claim 1 in which a mounting portion comprises a post formed with a locking taper for receipt in the bore of an implant having a matching locking taper.

5. An abutment according to claim 1 in which the mounting portion comprises a post formed with a thread for threaded engagement with a corresponding thread in a bore of an implant.

6. An abutment according to claim 1 in which the locking step extends over only a portion of the circumference of the mounting post.

7. An abutment for use with an implant placed in a bone of a patient comprising a mounting portion for receipt in an implant, a central portion having a smoothly curved outer surface and a prosthetic mounting post extending from the central portion, the post being generally cylindrical and tapered along a selected length of the post, the selected length having a first axial length portion and a second axial length portion, each axial length portion having a decreasing circumference as the distance from the central portion increases, the post formed with a locking step disposed intermediate to the first and second axial length portions with one side of the step being outboard, further from the central portion and an opposite side of the step being inboard, closer to the cental portion, the post having increased circumference on the outboard side of the step immediately adjacent to the step relative to the circumference on the inboard side of the step immediately adjacent to the step, the step being formed at a given distance from the central portion, a sleeve member having first and second ends formed with a bore extending from the first to the second end, the bore formed with a taper generally matching that of the prosthetic mounting post and with the first end receivable on the central portion of the abutment, the sleeve member having a distance selected from the first to the second ends so that the second end is disposed closely adjacent the locking step on the inboard side of the mounting post closer to the central portion when the first end of the sleeve member is received on the central portion of the abutment and the bore of the sleeve member at the second end having a circumference matching that of the mounting post at the inboard side of the step.

8. An abutment according to claim 7 in which the mounting post is formed with at least one anti rotational flat on the outer periphery thereof and the bore of the sleeve member is formed with a matching anti rotational flat.

9. An abutment according to claim 7 in which the central portion of the abutment is formed with a frustoconical shaped foot portion and the first end of the sleeve member is formed with a complimentary shaped foot portion which leads into the bore of the sleeve member and the outer surface of the sleeve member forms a smooth curved surface which merges confluently with the outer surface of the abutment.

10. An abutment according to claim 9 in which the outer surfaces of the central portion and the sleeve member are convex.

11. An abutment according to claim 7 in which at least a portion of the bore at the second end of the sleeve member is circular having a selected diameter and at least a portion of the circumference of the prosthetic mounting post is circular with a diameter of the post at the inboard side of the locking step immediately adjacent to the locking step being slightly smaller than the selected diameter and the diameter of the post at the outboard side of the locking step immediately adjacent to the locking step being slightly larger than the selected diameter.

12. An abutment according to claim 11 in which the difference in the selected diameter and the diameters of the post immediately adjacent to the locking step is in the range of approximately two to eight hundred thousandths mm.

13. An abutment according to claim 7 in which at least a portion of the bore at the second end of the sleeve member is circular having a diameter of between approximately 0.122 and 0.124 mm and at least a portion of the circumference of the prosthetic mounting post is circular with a diameter at the inboard side immediately adjacent to the locking step of between approximately 0.117 and 0.121 mm and at the outboard side immediately adjacent to the locking step of between approximately 0.123 and 0.125 mm.

14. An abutment according to claim 7 in which the second end of the sleeve member is formed with a locking interface for a second sleeve member.

15. An abutment according to claim 14 in which the sleeve member has a smooth outer surface configuration and a second end face and having a selected circumference at the second end face of the sleeve member and the locking interface comprises a longitudinally extending hub extending from the second end face of the sleeve member, the hub having a circumferentially extending groove between the second end face and a radially extending flange, the radially extending flange having a circumference less than the circumference of the outer surface configuration at the second end face and further comprising a second sleeve member having first and second ends, the first end formed with a flange receiving recess having a configuration complimentary to the flange and a lip being formed between the flange receiving recess and the first end of the second sleeve member, the lip having a dimension selected to create an interference fit with the flange.

16. An abutment according to claim 15 in which the flange is formed with a bevel on the side of the flange opposed to the groove to facilitate placement of the flange in the flange receiving recess.

17. An abutment according to claim 15 in which the first end of the second sleeve is formed with a bevel leading to the lip and another bevel is formed extending from the lip to the flange receiving recess.

18. An abutment according to claim 15 in which the second sleeve is formed with a bore extending therethrough and further comprising a pin having an elongated body having a configuration to closely fit in the bore of the second sleeve member to close the bore of the second sleeve member.

19. An abutment member according to claim 15 in which the second sleeve member has an outer surface configuration formed with an undercut portion to provide a locking mechanism.

20. An abutment according to claim 7 in which the sleeve member has an outer morphology corresponding to a selected tooth whereby the sleeve member can be modified to accommodate a specific clinical situation.

21. An abutment for use with an implant placed in a bone of a patient comprising a mounting portion for receipt in an implant, a central portion having a smoothly curved outer surface and a prosthetic mounting post extending from the central portion, the post being generally cylindrical having a longitudinal axis and tapered along a selected length of the post, the selected length having a first and a second axial length portion, each axial length portion having a decreasing circumference as the distance from the central portion increases, the post formed with a Locking step disposed intermediate to the first and second axial length portions with one side of the step being outboard, further from the central portion and an opposite side being inboard, closer to the central portion, the locking step extending an increased distance from the longitudinal axis on the outboard side immediately adjacent to the step relative to the distance from the longitudinal axis on the inboard side immediately adjacent to the step, the step being formed at a given distance from the central portion, a sleeve member having first and second ends formed with a bore extending from the first end toward the second end, the bore formed with a taper generally matching that of the prosthetic mounting post along at least a portion of the bore corresponding to the prosthetic mounting post from the central portion to the locking step with the sleeve slidably received on the prosthetic mounting post and the first end received on the central portion of the abutment, the bore formed with a retention surface receivable over the locking step for engagement with the inboard side of the locking step when the first end of the sleeve member is received on the central portion of the abutment.

22. An abutment according to claim 21 in which the retention surface is located at the second end of the sleeve member.

* * * * *